_United States Patent_ [19]

Callery et al.

[11] 4,034,100

[45] July 5, 1977

[54] ANTIHYPERTENSIVE AGENTS

[75] Inventors: Patrick S. Callery, Cockeysville; Nicolas Zenker, Lutherville; Jeremy Wright, Baltimore, all of Md.; Clement A. Stone, Blue Bell, Pa.

[73] Assignee: Merck & Co., Inc., Rahway, N.J.

[22] Filed: Feb. 13, 1976

[21] Appl. No.: 657,826

[52] U.S. Cl. .......................... 424/272; 260/307 C
[51] Int. Cl.² ..................................... C07D 263/58
[58] Field of Search ................ 260/307 C; 424/272

[56] References Cited
UNITED STATES PATENTS

| | | | |
|---|---|---|---|
| 3,190,797 | 6/1965 | Bindler et al. | 260/307 C |
| 3,268,546 | 8/1966 | Cain et al. | 260/307 C |

_Primary Examiner_—Raymond V. Rush
_Attorney, Agent, or Firm_—Daniel T. Szura; J. Jerome Behan

[57] ABSTRACT

Compounds of the formula

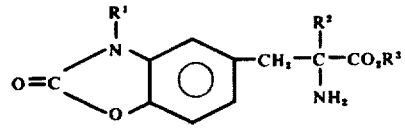

possess antihypertensive activity. Also provided are methods for the preparation of the compounds as well as pharmaceutical formulations and methods for their use as antihypertensive agents.

9 Claims, No Drawings

ANTIHYPERTENSIVE AGENTS

BACKGROUND OF THE INVENTION

This invention relates to antihypertensive agents and to methods for their preparation and use. More particularly, it relates to antihypertensive agents comprising a 3-(2-substituted-benzoxazol-5 -yl)-alanine compound and to methods for the preparation and use of the antihypertensive agents.

DESCRIPTION OF THE PRIOR ART

The art records a long search for agents that are effective in treating hypertensive patients with acceptable clinical results and few, if any, side effects. There are, of course, a number of products available commercially which are useful for this purpose. One that has been extremely effective for the treatment of hypertension is the L form of 3-(3,4-dihydroxyphenyl)-2-methylalanine. This compound and its method of use is described in U.S. Pat. No. 3,344,023, issued in 1967. While a number of other compounds are well known in the art as antihypertensive drugs, the search continues for even more effective agents.

The compositions of the present invention are also alanine derivatives as are those described above, but are distinctly different from prior art compounds in that they contain a 3-(2-substituted)benzoxazol-5-yl alanine.

OBJECTS OF THE INVENTION

It is, accordingly, an object of the present invention to provide new compounds that are useful as antihypertensive agents.

Another object is to provide antihypertensive agents that overcome or otherwise mitigate the problems of the prior art in this area.

A further object of the invention is to provide new benzoxazolone alanine compounds which exhibit antihypertensive activity as well as methods for preparation of these new compounds.

Another object is to provide pharmaceutical compositions for administering these benzoxazolone alanine compounds.

A still further object of the invention is to provide methods for the treatment of subjects suffering from hypertension.

These and other objects and advantages of the present invention will become apparent from the following description.

SUMMARY OF THE INVENTION

In satisfaction of the foregoing objects and advantages, there are provided by this invention novel antihypertensive agents of the following general formula:

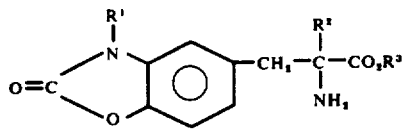

wherein each R is hydrogen or alkyl of from 1 to about 3 carbon atoms. The foregoing general formula is intended to include the racemic mixtures, the D and L enantiomorphs, and the pharmaceutically acceptable carboxylic salts and acid-addition salts. Also provided are methods for the preparation of the compounds of the foregoing general formula, as well as pharmaceutical formulations, and methods for their use in the treatment of subjects suffering from hypertension to effect blood pressure lowering in these subjects.

DESCRIPTION OF PREFERRED EMBODIMENTS

As pointed out above, the invention is concerned with new antihypertensive agents which have been found to have antihypertensive activity and thus are suitable for lowering the blood pressure of subjects suffering from hypertension. The antihypertensive agents may be best described as comprising a compound of the following general structural formula

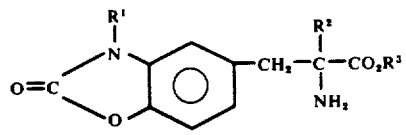

wherein each R is hydrogen or alkyl of from 1 to 3 carbon atoms.

Specific compounds of the present invention include the following:

2-amino-3-(2-oxo-2H-benzoxazol-5-yl)propionic acid;

2-amino-2-methyl-3-(2-oxo-2H-benzoxazol-5-yl)-propionic acid;

2-amino-3-(3-methyl-2-oxo-2H-benzoxazol-5-yl)-propionic acid;

2-amino-2-methyl- 3-(3-methyl-2-oxo-2H-benzoxazol-5-yl) propionic acid.

The compounds of the present invention wherein $R^1$ is hydrogen may be prepared by hydrogenating 3-nitro tyrosine to yield 3-aminotyrosine and reacting the latter with phosgene. The compounds of the present invention wherein $R^1$ is alkyl may be prepared by reductive alkylation of the alkyl ester of O,N-diacyl-3-nitrotyrosine followed by hydrolysis to produce the 3-alkylaminotyrosine compound and treating the latter with phosgene. These reactions take place under standard conditions.

The compounds of the present invention have been found to be effective in reducing elevated blood pressure in mammalian species, e.g., rats, and so are useful as antihypertensive agents. The compounds of the present invention are active in combination with α-hydrazino-α-loweralkyl-3,4-dihydroxyphenyl propionic acid or its salts loweralkyl-3,4-dihydroxyphenyl propionic acid or its salts or lower alkyl esters which compounds are themselves ineffective in reducing blood pressure in mammalian species. The compounds may be administered either orally or parenterally and they can be compounded by the usual pharmaceutical methods for use in the lowering of blood pressure in subjects suffering from hypertension. Dosage units for the compounds may vary from about 0.05 to about 100 mg per kg per day. Normal dosage units for the compounds for oral administration will vary from about 10 to about 500 mg per kg per day. For oral administration to humans the dosage range is from about 0.1 to about 5 grams per day, preferably from about 0.5 to about 1.5 grams per day, usually in small but frequent doses, e.g. in from 1 4 doses per day.

The antihypertensive agents of the present invention in the described dosages may be administered orally, however, other routes such as intraperitoneally, subcutaneously, intramuscularly or intravenously, may be employed.

For oral therapeutic administration, the active compounds of this invention may be incorporated with excipients and used in the form of tablets, troches, capsules, elixirs, suspensions, syrups, wafers, chewing gums, and the like. The amount of active compound in such therapeutically useful compositions or preparations is such that a suitable dosage will be obtained.

The tablets, troches, pills, capsules and the like may also contain the following: a binder such as gum tragacanth, acacia, corn starch or gelatin; and excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. Various other materials may be present as coatings or to otherwise modify the physical form of the dosage unit, for instance, tablets, pills or capsules may be coated with shellac, sugar, or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

As to the pharmaceutically acceptable salts, those coming within the purview of this invention include the pharmaceutically acceptable acid-addition salts. Acids useful for preparing these acid-addition salts include, inter alia, inorganic acids, such as hydrochloric, hydrobromic, sulfuric, and phosphoric acids, and organic acids such as maleic, fumaric, tartaric, citric, 2-acetoxybenzoic, salicylic, succinic, or methanesulfonic acids. The following examples illustrate the present invention without, however, limiting the same thereto. All temperatures are expressed in degrees Celsius.

EXAMPLE 1

2-Amino-3-(2-oxobenzoxazol-5-yl)propionic Acid Hydrochloride

A solution of 3-nitrotyrosine (5.0 g., 22.1 mmole) in 100 ml of acetic acid is shaken overnight with hydrogen (initial pressure 35 psi) and 10% palladium on charcoal catalyst. The suspension is filtered through a bed of diatomaceous earth and the solvent removed under vacuum. Phosgene gas is bubbled (approx. 60 ml/min.) through a solution of the residue in 1N HC 1 (100 ml) for 1 hour. The precipitate which develops upon cooling is collected and recrystallized from methanol/ether, m.p. 265°(decomp).

EXAMPLE 2

2-Amino-2-methyl-3-(2-oxobenzoxazol-5-yl) propionic Acid Hydrochloride

By following the procedure of Example 1, but substituting 2-amino-2-methyl-3-(3-nitro-4-hydroxyphenyl) propionic acid for 3-nitrotyrosine, the title compound is obtained.

EXAMPLE 3

2-Amino-3-(3-methyl-2-oxo-2H-benzoxazol-5-yl)propionic Acid Hydrochloride

3-Nitrotyrosine (5.0 g) is refluxed with a slight excess of acetyl chloride for 1 hour. The resulting product is then esterified by contact with an excess of methanol under acidic conditions. On evaporation of the excess alcohol, the methyl ester of O,N- diacetyl-3-nitrotyrosine is recovered. Reductive alkylation of this product with hydrogen, formaldehyde, sodium acetate and Raney nickel catalyst (J. Amer. Chem. Soc., 62, 69 (1940) produces the 3-methylamino product. This product is held at reflux with 10% HCl for 2 hours, cooled, and then treated with phosgene gas by the procedure of Example 1 to produce the title compound.

EXAMPLE 4

2-Amino-2-methyl-3-(3-methyl-2-oxo-2H-benzoxazol-5-yl) propionic acid

By following the procedure of Example 3 but substituting 3-nitro-α-methyltyrosine for 3-nitrotyrosine, the title compound is obtained.

EXAMPLE 5

2-Amino-3-(2-oxobenzoxazol-5-yl) propionic acid methyl ester

The product from Example 1 (0.1 mole) is held at reflux in 1500 ml of methanol saturated with HCl gas for 6 hours. The alcoholic solution is evaporated to yield a product which is recrystallized from water or methanol:ether to yield the title compound.

What is claimed is:

1. A compound of the formula:

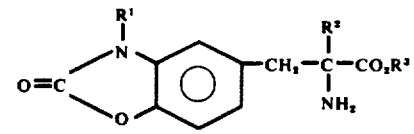

wherein each of R', R² and R³ is hydrogen or alkyl of from 1 to 3 carbon atoms, and the pharmaceutically acceptable acid-addition salts thereof.

2. A compound according to claim 1 wherein each of R', R² and R³ is hydrogen or methyl.

3. A compound according to claim 1 which is 2-amino-3-(2-oxo-2H-benzoxazol-5-yl)propionic acid;
2-amino-2-methyl-3-(2-oxo-2H-benzoxazol-5yl)propionic acid;
2-amino-3-(3-methyl-2-oxo-2H-benzoxazol-5-yl)propionic acid; or
2-amino-2-methyl-3-(3-methyl-2-oxo-2H-benzoxazol-5yl) propionic acid.

4. A compound according to claim 1 which is 2-amino-3-(2-oxo-2H-benzoxazol-5-yl)propionic acid.

5. A compound according to claim 1 which is 2-amino-2-methyl-3-(2-oxo-2H-benzoxazol-5yl)propionic acid.

6. A compound according to claim 1 which is 2-amino-3-(3-methyl-2-oxo-2H-benzoxazol-5yl)propionic acid.

7. A compound according to claim 1 which is 2-amino-2-methyl-3-(3-methyl-2-oxo-2H-benzoxazol-5yl) propionic acid.

8. A method for the treatment of hypertension in a mammalian species which comprises administering to a hypertensive subject an effective amount of a compound of claim 1.

9. A composition for treating hypertension comprising a compound of claim 1 as the active ingredient in combination with a pharmaceutically acceptable carrier.

* * * * *